(12) United States Patent
Fang et al.

(10) Patent No.: US 8,034,596 B2
(45) Date of Patent: Oct. 11, 2011

(54) METHOD FOR PRODUCING CELLULASE AND HEMICELLULASE HAVING HIGH HYDROLYTIC ACTIVITY

(75) Inventors: Xu Fang, Hiroshima (JP); Shinichi Yano, Hiroshima (JP); Hiroyuki Inoue, Hiroshima (JP); Shigeki Sawayama, Hiroshima (JP); Naoyuki Okuda, Tokyo (JP); Masanori Sato, Tokyo (JP); Masashi Kuroda, Tokyo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 12/598,694

(22) PCT Filed: Jul. 31, 2007

(86) PCT No.: PCT/JP2007/065322
§ 371 (c)(1),
(2), (4) Date: Nov. 3, 2009

(87) PCT Pub. No.: WO2008/139641
PCT Pub. Date: Nov. 20, 2008

(65) Prior Publication Data
US 2010/0136618 A1 Jun. 3, 2010

(30) Foreign Application Priority Data
May 7, 2007 (JP) ................. 2007-122694

(51) Int. Cl.
*C12N 1/00* (2006.01)
*C12N 9/14* (2006.01)
(52) U.S. Cl. ................... 435/195; 435/254.1
(58) Field of Classification Search ............ 435/183, 435/252.3, 195, 254.1
See application file for complete search history.

(56) References Cited

U.S. PATENT DOCUMENTS
4,742,005 A  5/1988  Yamanobe et al.
4,956,291 A  9/1990  Yamanobe et al.

FOREIGN PATENT DOCUMENTS
EP  0 913 467 A1  5/1999
JP  59-166081      9/1984
JP  61-162177      7/1986
JP  2003-135052    5/2003
WO  WO 99/11767    3/1999

OTHER PUBLICATIONS

International Search Report PCT/JP2007/065322 dated Aug. 28, 2007.
Supplementary European Search Report EP 07 79 1995.9 dated May 12, 2010.
Yuko Ikeda et al., "Efficient Cellulase Production by the Filamentous Fungus *Acremonium cellulolytikus*", Biotechnol. Prog. 2007, 23, 333-338.
Takashi Yamanobe et al., "Improvement of Fungal Strain Y-94 a Celllulolytic Enzyme Hyperproducer, and Enzymatic Saccharification of Exploded Wood", Agric. Biol. Chem. 54(2) 535-536, 1990.
Takashi Yamanobe et al., "Isolation of a Cellulolytic Enzyme Producing Microorganism, Culture Conditions and Some Properties of the Enzyme", Agric. Biol. Chem. 51 (1), 65-74, 1987.
Xu Fang et al., "Cellulase and hemicellulase production by *Acremonium cellulolyticus* for hydrolysis of biomass", Abstracts/Journal of Biotechnology, 136S (2008) S290-5344.
Xu Fang et al., "Hydrolysis of Lignocellulosic Biomass for Bioethanol Production with the Cellulolytic Enzyme System from *Acremonium celluloyticus* and *Trichoderma Reesel*", Biomass Technology Research Center, National Institute of Advanced Industrial Science and Technology, 5th Biomass-Asia Workshop Dec. 4-5, 2008 XP002579693.
Xu Fang et al., "Lactose Enhances Cellulase Production by the Filamentous Fungus *Acremonium cellulolyticus*" Journal of Bioscience and Bioengineering vol. 106, No. 2, 115-120, 2008.
Joni Prasetyo et al., "Response of Cellulase Activity in pH-Controlled Cultures of the Filamentous Fungus *Acremonium cellulolyticus*", Appl. Biochem. Biotechnol, (2010) 162:52-61.

*Primary Examiner* — Maryam Monshipouri
(74) *Attorney, Agent, or Firm* — Stephen A. Bent; Foley & Lardner LLP

(57) ABSTRACT

The present invention provides a novel cellulase-producing fungus, i.e. *Acremonium cellulolyticus* CF-2612 strain or a mutant thereof, which has an ability to produce cellulase so highly, a method for producing cellulase and/or hemicellulase by culturing said fungus, and a method for degrading or saccharifying biomass using the cellulase and/or hemicellulase.

10 Claims, 2 Drawing Sheets

METHOD FOR PRODUCING CELLULASE AND HEMICELLULASE HAVING HIGH HYDROLYTIC ACTIVITY

FIELD OF THE INVENTION

The present invention relates to the *Acremonium cellulolyticus* CF-2612 strain or a mutant thereof, which is a novel microorganism belonging to the genus *Acremonium* and has an ability to produce cellulase so highly.

The present invention also relates to a method for producing cellulase and/or hemicellulase using the microorganism, and to a method for degrading or saccharifying biomass using the cellulase and/or hemicellulase.

BACKGROUND OF THE INVENTION

The "cellulase" is a collective name denoting the enzyme group that catalyzes an enzyme reaction system in which cellulose is hydrolyzed into glucose, cellobiose, or cellooligotose. Depending on the catalytic mechanism, there are enzymes referred to as FPase, CMCase, cellobiase, and the like. Cellulase degrades cellulose into glucose as an end product of degradation via interaction among such enzymes.

The "hemicellulase" is a collective name denoting the enzyme group that catalyzes an enzyme reaction system in which hemicellulose is hydrolyzed into xylose, arabinose, mannose, galactose, or the like. Depending on the catalytic mechanism, there are enzymes referred to as xylanase, arabinanase, arabinofuranosidase, mannanase, galactanase, xylosidase, mannosidase, and the like.

Hitherto, microorganisms such as *Trichoderma reesei* (Biotechnol. Bioeng., 23, 1837-1849 (1981)), *Trichoderma viride* (*T. viride*) (Appl. Biochem. Biotechnol., 57-58, 349-360 (1996)), and microorganisms belonging to the genera *Aspergillus, Penicillium*, and the like, have been used as cellulase-producing fungi for producing cellulase and/or hemicellulase, which can be used for saccharification of lignocellulose biomass. However, by use of such microorganisms, satisfied productivity of cellulase was not able to be achieved, which was a drawback. In addition, the produced cellulase did not have a sufficient ability to degrade cellulose, meaning that the known cellulose enzymes cannot completely degrade cellulose into glucose. Accordingly, there is a problem that a large amount of cellobiose and cellooligosaccharide, which are intermediates, are produced and remains during the degradation of cellulose.

To solve the above-mentioned problems, it has been attempted to intensively isolate from the nature, microorganisms which have a high ability to produce cellulase and an ability to produce cellulase having high activity. As a result, a microorganism belonging to *Acremonium cellulolyticus*, which can substantially completely degrade cellulose into glucose, was isolated from soil by us (JP 59-166081 A (1984)). We have further found that the mutant *Acremonium cellulolyticus* C1 strain (FERM P-18508) had a higher ability to produce cellulase when compared with said parent microorganism (JP 2003-135052 A).

In recent years, there has been a great interest in that biomass is subjected to enzymatic degradation and saccharification using cellulase and/or hemicellulase to convert it into constituent units like glucose, xylose, arabinose, mannose, and galactose, which are used to produce fermentation products such as ethanol and lactic acid that can be utilized as a liquid fuel or chemicals. Thus, the development of a technology for practical application of biomass has been carried out actively. Hence, for the purpose of an economical and practical use of biomass, there is a great demand on microorganisms with an ability to produce cellulase more highly than the known cellulase-producing fungi as described above.

Under the above-described circumstances, it is an objective of the present invention to efficiently produce cellulase and/or hemicellulase and to efficiently degrade or saccharify biomass, through improving the ability to produce cellulose in cellulase-producing microorganisms.

SUMMARY OF THE INVENTION

As a result of intensive studies to achieve the above objectives, we have now found that the *Acremonium cellulolyticus* CF-2612 strain, which has been obtained as a mutant of the *Acremonium cellulolyticus* C1 strain (FERM P-18508), had higher cellulase activities, in particular such as FPase, cellobiase and avicelase activities, than those of the C1 strain, as well as a higher ability to produce cellulase. This has led to the completion of the present invention.

The present invention is characterized as follows.

(1) An *Acremonium cellulolyticus* strain selected from the group consisting of *Acremonium cellulolyticus* CF-2612 strain (FERM BP-10848) and mutants thereof, characterized in that said strain has an ability to produce cellulase more highly than the known *Acremonium cellulolyticus* C1 strain (FERM P-18508).

(2) A method for producing cellulase and/or hemicellulase, comprising culturing the *Acremonium cellulolyticus* strain of (1) above, which is a cellulase-producing fungus, in a culture medium, and collecting the cellulase and/or hemicellulase from the culture or culture medium.

(3) A method for saccharifying biomass, comprising culturing the *Acremonium cellulolyticus* strain of (1) above, which is a cellulase-producing fungus, in a culture medium, and saccharifying or degrading the biomass in the culture or culture medium containing cellulase and/or hemicellulase.

(4) The method of (2) or (3) above, wherein the carbon source used in the medium is selected from the group consisting of powdery cellulose, avicel, cellobiose, filter papers, general papers, waste papers, wood, wheat bran, straw, rice straw, rice husks, bagasse, soybean cake, soybean curd residues, coffee bean residues, rice bran, lactose, lactose hydrate, whey, dairy products, hydrolysis residues, and mixtures thereof.

(5) The method of (2) or (3) above, wherein the culture is a liquid culture or solid culture.

(6) The method of (2) or (3) above, wherein the cellulase is FPase, CMCase, avicelase, cellobiase, or a mixture thereof.

(7) The method of (2) or (3) above, wherein the hemicellulase is xylanase, arabinanase, arabinofuranosidase, mannanase, galactanase, xylosidase, mannosidase, or a mixture thereof.

(8) A method for degrading or saccharifying biomass, comprising degrading or saccharifying the biomass using cellulase and/or hemicellulase obtained by the method of (2) above.

According to the present invention, the cellulase productivity can be highly improved with the use of the *Acremonium cellulolyticus* CF-2612 strain, which is a novel microorganism belonging to the genus *Acremonium* and having a high ability to produce cellulase. Additionally, biomass can be efficiently degraded or saccharified by use of cellulase and/or hemicellulase produced by such a microorganism. Thus, the present invention has such significant effects.

DETAILED DESCRIPTION OF THE INVENTION

Figure 1:
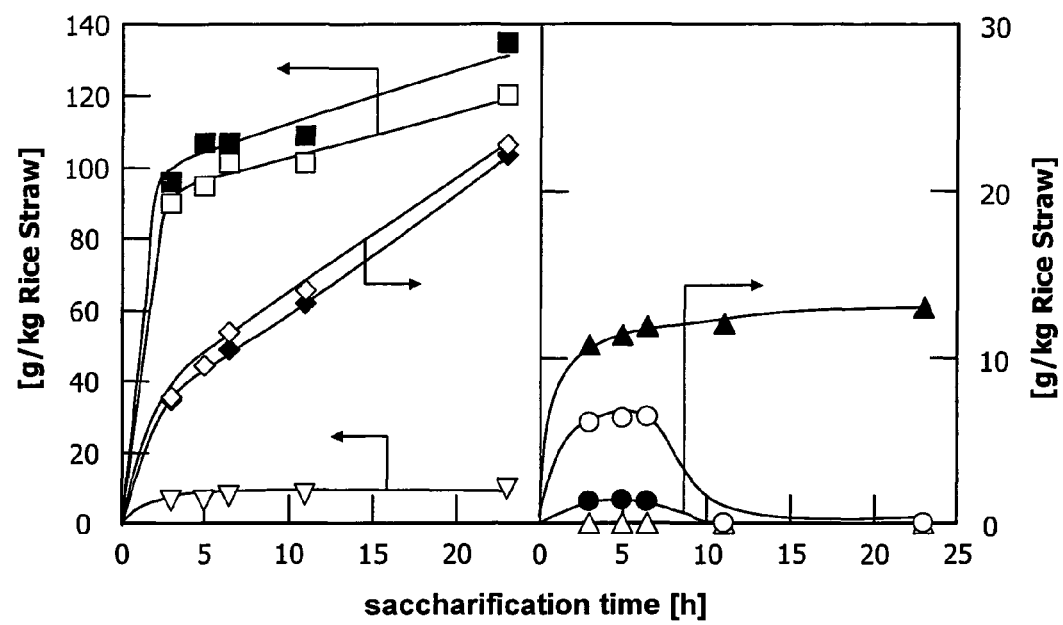
FIG. 1 shows the results of the experiments of saccharifying rice straw using the culture medium of the CF-2612 strain or the C1 strain. Symbols are as followed: closed symbol, the culture medium of the CF-2612 strain (17.7 FPU/ml); open symbol, the culture medium of the C1 strain (11.9 FPU/ml); "▼", control (wherein distilled water was added instead of the cultured medium in the same volume); "□", glucose; "◇", xylose; "△", arabinose; and "○", mannose.

Hereafter, the present invention will be described in detail.

The term "cellulase" as used herein is a collective name for enzymes involved in cellulose degradation, such as FPase, CMCase, avicelase and cellobiase as described above. In the invention, the cellulase encompasses any enzyme having an activity of degrading cellulose.

Cellulose is a glucose polymer in which glucose is highly polymerized via β-1,4 glucoside bonds, and it is found as a cell wall component in any types of plants.

The term "hemicellulase" as used herein is a collective name for enzymes capable of degrading hemicellulose. In addition, the hemicellulose excludes cellulose and pectin from among polysaccharides that constitute cell walls of terrestrial plant cells.

According to the present invention, the term "cellulase-producing fungus" encompasses microorganisms capable of producing cellulase and microorganisms capable of producing both cellulase and hemicellulase. Examples the microorganisms include fungi isolated from natural sources, mutants thereof, and genetic recombinant fungi derived therefrom. In the present invention, particularly preferable examples of the cellulase-producing fungus are the *Acremonium cellulolyticus* CF-2612 strain, which has been obtained as a mutant of the *Acremonium cellulolyticus* C1 strain, and mutants of the CF-2612 strain. The *Acremonium cellulolyticus* CF-2612 strain of the invention was deposited with the International Patent Organism Depositary in the National Institute of Advanced Industrial Science and Technology (AIST Tsukuba Central 6, 1-1, Higashi 1-chome, Tsukuba-shi, Ibaraki-ken 305-8566, Japan), under Accession No. FERM P-21290 on Apr. 10, 2007, which strain was then transferred to the international deposit under the term of the Budapest Treaty on Jul. 4, 2007 under Accession No. FERM BP-10848.

The term "ability to produce cellulase" as used herein refers to an ability by which cellulase is produced. The ability to produce cellulase becomes higher as the total enzyme activity of cellulase increases.

As used in the invention, the term "biomass" encompasses cellulose-based and/or lignocellulose-based biomass as produced by plants or algae. Examples of such biomass include, but are not limited to, wood, wheat bran, straw, rice straw, rice husks, bagasse, soybean cake, soybean curd residues, coffee bean residues, rice bran, and hydrolysis residues. The term "hydrolysis residues" as used herein refers to residues obtainable by hydrolysis treatment of the biomass with acids, enzymes, or the like.

As used in the invention, the "culture" method includes liquid cultures and solid cultures, but is not limited to said culture methods as long as selected microorganisms can be cultured.

As used in the invention, the term "to degrade or saccharify biomass" refers to degradation of cellulose and/or hemicellulose contained in biomass, thereby converting it into oligosaccharides, disaccharides, monosaccharides, or mixtures thereof. In other words, this term means hydrolysis of glycosidic bonds of polysaccharides with cellulase and/or hemicellulase.

(Preparation of a Mutant of a Cellulase-Producing Fungus)

A mutant of the cellulase-producing fungus can be obtained by irradiation treatment with ultraviolet or radioactive rays, or by treatment with chemicals (e.g., nitrous acid, base analogs (e.g., 5-bromouracil and 2-aminopurine), alkylating agents (e.g., nitrosoguanidine and ethyl methanesulfonate), acridine dyes (e.g., acriflavine and proflavine), carcinogens (e.g., 4-nitroquinoline-1-oxide), and antibiotics (e.g., mitomycin C)).

Alternatively, it is possible to obtain a mutant from the cellulase-producing fungus by genetic recombination. Specifically, fungal cells are disrupted in liquid nitrogen with the use of a mortar or the like, followed by extraction of total RNA by, for example, the phenol/chloroform method, the guanidium method, or the phenol/SDS method. If necessary, the RNA is allowed to pass through an oligo (dT) cellulose column such that poly(A)$^+$ RNA can be obtained. Alternatively, cDNA is produced from poly(A)$^+$ RNA by a known reverse transcription reaction. Primers are designed based on the known nucleotide sequence of cellulase, which sequence can be obtained by accessing a databank such as NCBI or GenBank. Then, the cellulase gene of the fungal cell is cloned by PCR using the above-described RNA or cDNA as a template. The cloned gene is ligated downstream of a promoter (such as pyr4 promoter or cbh1 promoter) that can induce high expression and/or of a secretory signal peptide, and thereafter the resultant DNA is inserted into a vector compatible with a host microorganism. Thus, a recombinant vector of interest can be produced. Such a vector may further comprise a terminator region, a variety of marker genes used for selection, such as antibiotic-resistant genes, or the like. Alternatively, when designing primers, mutation may be preliminarily induced in the nucleotide sequence of a primer, and PCR is carried out in the same manner as above using the primers, such that a mutated cellulase gene can be cloned. Then a recombinant vector can be produced with the use of the mutated cellulase gene. When the recombinant vector is introduced into a host microorganism by any of a variety of known gene transfer methods, such as the calcium treatment method, the gene injection (transfection) method, the particle gun method, or the electroporation method, it is possible to obtain a mutant. Examples of the host microorganism include, but are not limited to, microorganisms belonging to the genera *Acremonium*, *Trichoderma*, *Aspergillus*, *Penicillium*, and the like. In addition, molecular biological methods used in the above genetic recombination process can be carried out with reference to methods as described in K. Saigo and Y. Sano, the Japanese translation of "Short Protocols in Molecular Biology (third edition) I, II and II", edited by F. M. Ausubel et al., Maruzen, Tokyo, Japan (1997).

Screening for a mutant of the cellulase-producing fungus can be carried out by the following methods:

Method using a dye-bound cellulose (Cellulose Azure (Sigma)): A dye-bound cellulose is obtained by allowing a blue dye (Remazol Brilliant Blue R) to bind to cellulose. Upon degradation using cellulase, the dye is released and dispersed into a medium such that enzyme activity can be detected. A sample solution containing a mutant of the cellulase-producing fungus is applied to a Czapeck-Dox agar medium containing 0.5% to 1% Cellulose Azure, followed by culture at an adequate temperature for 5 to 7 days. Then, cells in a colony, around which a substrate is degraded and dispersed into the medium, resulting in halo formation, are recovered.

Method using acid-treated cellulose: Ice-cooled 60% $H_2SO_4$ (200 ml) is added to 50 g of cellulose powder. The resulting solution is agitated on ice until semitransparent viscous paste is obtained. Then, the resultant is allowed to stand for 1 hour. Ice-cooled acetone (2 L) is poured thereinto such that cellulose is precipitated. Then, the suspension of the obtained white precipitate is obtained using a Polytron homogenizer. The white precipitate contained in the suspension is recovered on a glass filter, followed by resuspension in 0.5 L of ice-cooled acetone. Then, the obtained suspension is washed by glass filter filtration. The thus recovered white precipitate is suspended in 300 mL of distilled water, followed by homogenization using Polytron homogenizer. Distilled water is added thereto such that the resulting solution (500 mL) is obtained. 1N NaOH is added to the solution to adjust the pH to a pH 5 to 6, followed by washing with 3 L of 75% acetone on a glass filter. Subsequently, the solvent is substituted with 99.5% ethanol and ether, followed by air drying. Thus, the acid-treated cellulose powder can be obtained. A sample solution containing a mutant of cellulase-producing fungus is applied to a Czapeck-Dox agar medium containing (1% to 2%) acid-treated cellulose, followed by culture at an adequate temperature for 5 to 7 days. Then, cells in a colony, around which acid-treated cellulose particles are degraded by cellulase, resulting in transparent halo formation, are recovered (Yutaka Kashiwagi, "Enzymes from Filamentous Fungi by Fermentation," Manual of Utilizing Microorganism Genetic Matter (16), the National Institute of Agrobiological Sciences (Tsukuba, Ibaraki, Japan), Feb. 29, 2004).

In addition to the above methods, the recovered fungal strain is further cultured, and the enzyme activity of cellulase produced in the culture supernatant is measured by methods as described below (in "measurement of cellulase activity"). Thus, it is possible to screen for a mutant of the cellulase-producing fungus, having a high enzyme activity.

(Culture of a Cellulase-Producing Fungus)

As is specifically described in the Examples below, it is possible to culture the cellulase-producing fungus or a mutant thereof.

The medium used for culturing the cellulase-producing fungus may comprise: carbon sources such as powder cellulose (including avicel), cellobiose, filter papers, general papers, waste papers, wood, wheat bran, straw, rice straw, rice husks, bagasse, soybean cake, soybean curd residues, coffee bean residues, rice bran, lactose, lactose hydrate, whey, dairy products, hydrolysis residues, and mixtures thereof; nitrogen sources such as inorganic ammonium salts (e.g., ammonium sulfate and ammonium nitrate) and nitrogen-containing organic materials (e.g., urea, amino acids, meat extracts, yeast extracts, polypeptone, and protein degradation products); and inorganic salts such as magnesium sulfate, potassium dihydrogen phosphate, potassium tartrate, zinc sulfate, magnesium sulfate, copper sulfate, calcium chloride, iron chloride, and manganese chloride. If necessary, a medium containing trace amounts of organic nutrients may be used. Also, a solid medium to which agar or gelatin has been added for solidification, a semifluid medium to which agar has been added at a low concentration, or a liquid medium containing medium components (i.e., bouillon or broth) alone may be used. The preferable medium is a liquid medium.

Culture temperature and culture time can vary depending on types of cellulase-producing fungi. In general, the culture can be carried out at a temperature ranging from about 28° C. to about 32° C. for a period of from about 48 hours to about 10 days.

Examples of a fermentation tank that can be used for culture include an aeration-agitation type tank, a bubble column tank, a fluid bed tank, and a packed bed tank.

Fungal cells are removed from the above culture medium by a known method involving centrifugation, filtration, or the like, such that the supernatant is obtained. The supernatant can be directly used as a crude enzyme solution.

(Purification of Cellulase and/or Hemicellulase)

Cellulase and/or hemicellulase can be purified from the above supernatant by any of the following known methods used for protein purification or by a combination of two or more of such methods: namely, salting-out with ammonium sulfate; separation by precipitation with an organic solvent (e.g., ethanol, methanol, or acetone); chromatography such as ion exchange chromatography, isoelectric chromatography, gel filtration chromatography, hydrophobic chromatography, adsorption column chromatography, affinity column chromatography on gel with substrate or antibody bound, or reverse-phase column chromatography; and filtration treatments such as microfiltration, ultrafiltration, and reverse osmosis.

(Immobilization of Cellulase and/or Hemicellulase)

Purified cellulase and/or hemicellulase may be immobilized. Immobilized cellulase and/or hemicellulase is generally so stable that it can be continuously and repeatedly used. Hence, the immobilized enzyme is advantageous. Immobilization of cellulase and/or hemicellulase can be carried out by a carrier binding method, a crosslinking method, or an entrapment method. According to the carrier binding method, cellulase and/or hemicellulase are/is allowed to bind to a water-insoluble carrier (e.g., polyacrylamide gel, polystyrene resin, porous glass, or metallic oxides) via physical adsorption, ionic binding, and covalent binding. According to the crosslinking method, the enzyme is immobilized by crosslinking therebetween via a reagent containing two or more functional groups. Examples of a crosslinking reagent that can be used include glutaraldehyde that forms a Schiff base, an isocyanic acid derivative that forms peptide bonds, N,N'-ethylene maleimide, bis-diazobenzene that forms diazo coupling, and N,N'-polymethylene-bis-iodacetamide that causes alkylation. The entrapment method involves lattice formation, in which cellulase and/or hemicellulase are/is incorporated into small lattices of polymer gel, or microcapsulation, in which cellulase and/or hemicellulase are/is encapsulated by a semipermeable membrane. In the case of the method involving lattice formation, a synthetic polymer substance such as polyacrylamide gel or polyvinyl alcohol or a polymer compound such as photo-curing resin may be used. In the case of the method involving microcapsulation, hexamethylenediamine, sebacoyl chloride, polystyrene, lecithin, or the like may be used (Saburo Hukui, Ichiro Chibata, Shuichi Suzuki, "Enzyme Engineering (Kohso Kogaku)," Tokyo Kagaku Dozin, Tokyo, Japan, 1981).

(Measurement of Cellulase Activity)

Cellulase activity can be measured by the following method. Substrate such as filter paper, carboxymethylcellulose (CMC), microcrystalline cellulose (Avicel), salicin, or cellobiose is added to the above supernatant or purified cellulase; the enzyme reaction is allowed to take place for a certain period of time; the Somogy-Nelson method and the DNS method are carried out for color development of the obtained reducing sugar; and colorimetric determination is carried out at a certain wavelength.

According to the Somogy-Nelson method, the Somogy copper reagent (Wako Pure Chemical Industries, Tokyo, Japan) is added to the above reaction mixture of after reaction for a certain period of time, thereby stopping the reaction. Then, the reaction mixture is boiled for about 20 minutes, followed by immediate cooling with the use of tap water. After cooling, the Nelson reagent is injected into the reaction mixture such that the reduced copper precipitate is dissolved, resulting in color development. The resultant is allowed to stand for about 30 minutes, following by addition of distilled water. Subsequently, absorbance is measured.

When the DNS method is used, an enzyme solution is added to a 1% CMC substrate solution, followed by carrying out the enzyme reaction for a certain period of time. The enzyme reaction is terminated by boiling or the like. Then, dinitrosalicylic acid is added to the reaction mixture, followed by boiling for 5 minutes. After cooling, absorbance is measured (Yutaka Kashiwagi, supra).

(Degradation or Saccharification of Biomass)

Known methods can be used as a technique for degrading or saccharifying any biomass. For instance, the biomass can be used either in a dry form or in a wet form. To elevate the processing speed, it is preferable to roughly disrupt or shred the biomass into sizes of 100 to 1000 μm before use. For this purpose, conventional machines, such as ball mill, vibration mill, cutter mill, hammer mill, Wiley mill, and jet mill, can be used. Thereafter, the biomass that has been roughly disrupted or shredded is suspended in an aqueous medium, followed by addition of a culture supernatant containing cellulase or hemicellulase or a combination thereof, or by addition of purified or immobilized cellulase and/or hemicellulase. The resultant is heated with agitation or shaking. Thus, the biomass can be degraded or saccharified. In the above method, the pH and temperature of the reaction mixture may be within such a scope that does not cause deactivation of cellulase and/or hemicellulase. In general, when the reaction is carried out under atmospheric pressure, the temperature can be from 5° C. to 95° C., and the pH can be from 1 to 11. For instance, the culture supernatant containing 0.25 to 1 L of an acetate buffer (0.05 M, pH 4.8) and 0.01 to 0.2 L of cellulase (e.g., 10 to 20 U/ml) or purified cellulase can be added to 50 g of disrupted rice straw. Then the resulting solution is agitated or shaken at 45° C. to 60° C., so that the biomass is degraded or saccharified. The enzyme reaction can also be carried out in a batch-wise or continuously.

EXAMPLES

The present invention will hereafter be described in more detail by the following examples, but the scope of the present invention is not limited thereto.

*Acremonium cellulolyticus* CF-2612 Strain (Hereafter, Referred to as the CF-2612 Strain)

(1) Method for Obtaining the CF-2612 Strain

A parent strain (*Acremonium cellulolyticus* C1 strain (FERM P-18508; hereafter referred to as the C1 strain)) was subjected to aerobic culture at 30° C. for 24 hours, followed by irradiation of ultraviolet rays (UV). Then, the resultant cells were incubated at 30° C. Mutant strains having a higher activity were screened from the grown colonys, followed by a second mutation of the first mutant strains, which was carried out by the same method. Then, mutant strains having a higher activity than the previous ones were screened, which were then subjected to a third mutation by NTG treatment. Thus, the mutant CF-2612 strain was obtained. The CF-2612 strain has the following morphological properties.

(2) Morphological Properties of the CF-2612 Strain Upon Culture

The CF-2612 strain and the C1 strain were separately cultured on 3 types of selective agar media for 7 to 14 days for observation of morphologic properties. The results are shown below.

[Culture on Carbon Source-Containing Selective Agar Medium A]

(Selective Medium A)
  Glucose 50 g/L
  Ammonium sulfate 5 g/L
  Urea 2 g/L
  Magnesium sulfate 1.2 g/L
  Potassium dihydrogen phosphate 24 g/L
  Potassium tartrate 4.7 g/L
  Zinc sulfate 10 mg/L
  Manganese sulfate 10 mg/L
  Copper sulfate 9 mg/L
  Tween80 1 g/L
  Agar 20 g/L
  pH 4.0

The visual observation of the colonys of the C1 and CF-2612 strains cultured on the selective medium A showed that the C1 strain had a light red-brownish, flocculent and slowly standing-out appearance, while the CF-2612 strain grew to form a highly angular shape with many pomegranate-capsule-like corrugations. The colony diameter differed between their colonys: namely, 18-20 mm for the C1 strain and 10-13 mm for the CF-2612 strain.

[Culture on Selective Agar Medium B]

(Selective Medium B)

The medium used was prepared by removing glucose from the carbon source of selective medium A and instead adding the following:
  cellulose powder 25 g/L; and
  carboxymethylcellulose (CMC) 25 g/L.

The visual observation of the colonys of the C1 and CF-2612 strains cultured on the selective medium B showed that the C1 strain had a flocculent, slowly standing-out appearance or radial wrinkles on the surface, while the CF-2612 strain had smooth irregular wrinkles but not white flocculent hypha. The diameter differed between their colonys: namely, 15-18 mm for the C1 strain and 10-13 mm for the CF-2612 strain.

[Culture on Potato Dextrose-Containing Agar Medium]

(Potato Dextrose Agar Medium)
  Potato percolate 4 g/L
  Glucose 20 g/L
  Agar 15 g/L
  pH 5.6±0.2

The visual observation of the colonys of the C1 and CF-2612 strains cultured on the potato dextrose-containing agar medium showed that the colony of the C1 strain was 18-20 mm in diameter and had an obviously standing-out, doughnut-like shape which has a centeral hole. In addition, this colony tended to permeate toward the bottom portion of the medium and had a white mycelial bunch formed on the red-brownish colony. On the other hand, in the CF-2612 strain, the colony was 10-13 mm in diameter and had no centeral hole. In addition, deep wrinkles were formed and thus white ridges appeared on the colony.

Comparison of Enzyme Activity Between the CF-2612 Strain and the C1 Strain

The CF-2612 strain and the C1 strain were compared with each other in terms of the enzyme activity of cellulase. A medium (for culture of a cellulase-producing fungus) with the following composition was sterilized by a conventional method and was then inoculated with fungal cells of each strain, followed by aerobic culture at 30° C. for 7 days. The supernatant obtained by centrifugation of the culture was subjected to measurement of the enzyme activity of the produced cellulase.

(Composition of Medium)
Cellulose powder 50 g/L
Ammonium sulfate 5 g/L
Urea 4 g/L
Magnesium sulfate 1.2 g/L
Potassium dihydrogen phosphate 24 g/L
Potassium tartrate 4.7 g/L
Zinc sulfate 10 mg/L
Manganese sulfate 10 mg/L
Copper sulfate 10 mg/L
Tween 80 1 g/L
pH 4.0

The above measurement of enzyme activity was carried out by the following method.

[Assay of Enzyme Activity]

FPase: Filter paper (Whatman No. 1, 1×6 cm) was used as a substrate. The adequately diluted culture supernatant 0.5 mL and citrate buffer (pH 4.8, 0.05 M) 1.0 mL were added to the substrate, followed by enzyme reaction at 50° C. for 1.0 hour. Then, 3.0 mL of dinitrosalicylic acid reagent was added, followed by heating at 100° C. for 5 minutes for color development. After cooling, 200 μl of the resultant was added to 2.5 mL of distilled water, followed by colorimetry at a wavelength of 540 nm. Herein, the enzyme amount at which reducing sugar is produced in an amount corresponding to 1 μmmol of glucose per minute was defined as 1 unit (U).

CMCase: The adequately diluted enzyme solution and 2% carboxymethylcellulose sodium solution (dissolved in citrate buffer (pH 4.8, 0.05 M)) were mixed in equal volumes, followed by enzyme reaction at 50° C. for 30 minutes. Then, 3.0 mL of dinitrosalicylic acid reagent was added, followed by heating at 100° C. for 5 minutes for color development. After cooling, 200 μl of the resultant was added to 2.5 mL of distilled water, followed by colorimetry at a wavelength of 540 nm. Herein, the enzyme amount at which reducing sugar is produced in an amount corresponding to 1 μmol of glucose per minute was defined as 1 unit (U).

Avicelase: The adequately diluted enzyme solution and 1 ml of acetate buffer (pH 4.8, 0.1 M) containing 10 mg of avicel were mixed in equal volumes, followed by enzyme reaction at 50° C. for 2 hours. Then, 3.0 mL of dinitrosalicylic acid reagent was added, followed by heating at 100° C. for 5 minutes for color development. After cooling, 200 μl of the resultant was added to 2.5 mL of distilled water, followed by colorimetry at a wavelength of 540 nm. Herein, the enzyme amount at which reducing sugar is produced in an amount corresponding to 1 μmol of glucose per minute was defined as 1 unit (U).

Cellobiase activity: The adequately diluted enzyme solution and 1 mL of 15 mM cellobiose solution in citrate buffer (pH 4.8, 0.05 M) were mixed in equal volumes, followed by enzyme reaction at 50° C. for 30 minutes. Then, the enzyme reaction was terminated by heating at 100° C. for 5 minutes. The glucose concentration in the solution was measured using a laboratory test kit (Glu-CII, Wako Pure Chemicals, Tokyo, Japan). Herein, the enzyme amount at which reducing sugar is produced in an amount corresponding to 2 μmol of glucose or 1 μmol of cellobiose per minute was defined as 1 unit (U).

The results are shown in table 1.

TABLE 1

| Strain | FPase [U/ml] | CMCase [U/ml] | Avicelase [U/ml] | Cellobiase [U/ml] |
| --- | --- | --- | --- | --- |
| C1 | 11.90 | 76.59 | 2.63 | 21.91 |
| CF-2612 | 17.71 | 64.92 | 5.49 | 38.63 |

From Table 1, it is understood that the total enzyme activity of cellulase contained in the supernatant obtained from the culture of the CF-2612 strain was higher than that of the C1 strain, and that the activity levels of, in particular, FPase, cellobiase, and avicelase were significantly high. This suggests that the CF-2612 strain has an ability to produce such enzymes more highly than the C1 strain.

Comparison of Saccharification Effect Between the CF-2612 Strain and the C1 Strain With the use of the above culture media of the CF-2612 strain and the C1 strain, the strains were compared with each other in respect of their saccharification effects.

(Composition of Reaction Mixture)
Distilled water 0.7 ml
0.5 M acetate buffer (pH 4.8) 0.1 ml
Rice straw or eucalyptus powder (which was disrupted for 4 hours using ball mill) 50 mg Culture media of the CF-2612 strain and the C1 strain (0.2 ml each) were separately added to the above reaction mixture to react at 45° C.

FIG. 1 shows experimental results in the case that rice straw was used for the reaction mixture. The saccharification experiment of rice straw showed that the amount of glucose produced in the culture medium of the CF-2612 strain was greater than that of the culture medium of the C1 strain, indicating that the rate of saccharification (or % saccharification) of the CF-2612 strain is higher. Furthermore, when the culture medium of the CF-2612 strain was used for saccharification, arabinose was produced; however, when the culture medium of the C1 strain was used for saccharification, no arabinose was found in the saccharified solution. This suggests that arabinanase and/or arabinofuranosidase were contained in the culture medium of the CF-2612 strain, whereas neither arabinanase nor arabinofuranosidase was contained in the culture medium of the C1 strain.

Figure 2:
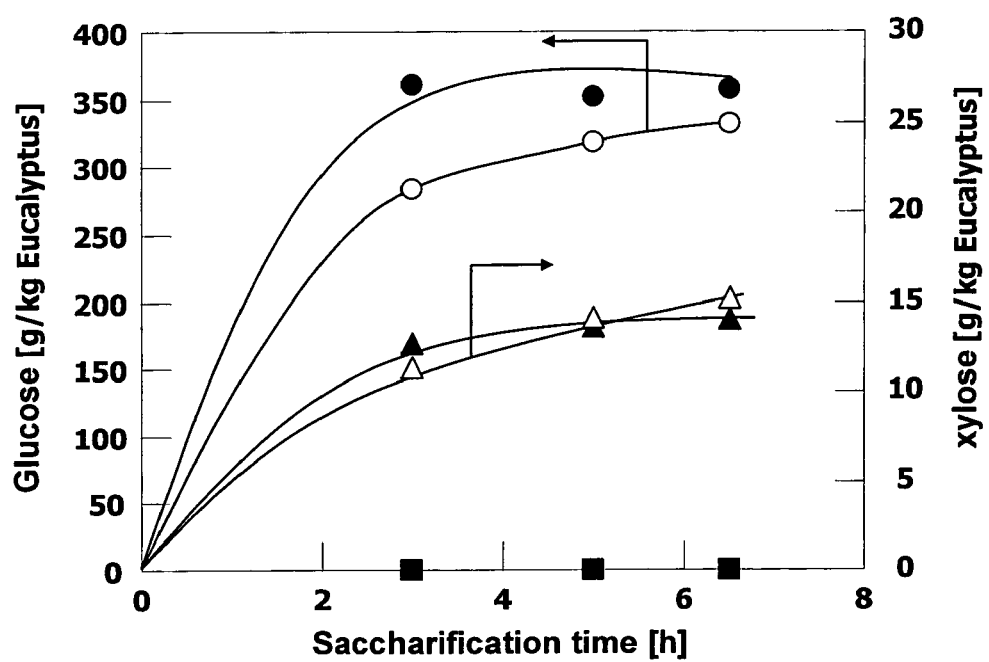
FIG. 2 shows the results of the experiments of saccharifying eucalyptus powder using the culture medium of the CF-2612 strain or the C1 strain. Symbols are as followed: closed symbol, the cultured medium of the CF-2612 strain (17.7 FPU/ml); open symbol, the cultured medium of the C1 strain (11.9 FPU/ml); "■", control (wherein distilled water was added instead of the cultured medium in the same volume); "○", glucose; and "△", xylose.

FIG. 2 shows the experimental results in the case that eucalyptus powder was used as the substrate. This experiment showed that the amount of glucose produced in the culture medium of the CF-2612 strain was greater than that of the culture medium of the C1 strain, indicating that the rate of saccharification (or % saccharification) of the 2612 strain is higher.

Thus, these results show that the CF-2612 strain has a greater saccharification effect than the C1 strain, and that the CF-2612 strain differs from the C1 strain in that the CF-2612 strain has the ability to produce arabinanase and/or arabinofuranosidase.

Scale-Up Culture of the CF-2612 Strain

The medium (for the culture of a cellulase-producing fungus) with the composition as described below was sterilized by conventional method. A preculture of the CF-2612 strain (50 mL) was subjected to aerobic shake culture at 30° C. for 3 days. The same medium (0.95 L) was inoculated with the preculture (50 mL), and then the aerobic culture was carried out in a jar fermenter at 30° C. for 5 days. Thereafter, 40 g/L cellulose powder and 2 g/L urea were added, followed by culture for 2 days. The resultant culture was centrifuged to obtain the supernatant, which was tested for FPase activity in the manner as above. As a result, the enzyme activity of the produced FPase reached 26.1 U/ml.

(Composition of Medium)
Cellulose powder 60 g/L (40 g/L in preculture)
Ammonium sulfate 5 g/L
Urea 4 g/L (2 g/L in preculture)
Magnesium sulfate 1.2 g/L
Potassium dihydrogen phosphate 24 g/L
Potassium tartrate 4.7 g/L
Zinc sulfate 10 mg/L
Manganese sulfate 10 mg/L
Copper sulfate 10 mg/L
Tween 80 1 g/L
pH 4.0

INDUSTRIAL APPLICABILITY

The *Acremonium cellulolyticus* CF-2612 strain of the present invention has a high ability to produce cellulase, indicating that cellulase can be efficiently produced with the use of this strain. According to the present invention, biomass can advantageously be degraded or saccharified economically and efficiently using the produced cellulase and/or hemicellulase.

The invention claimed is:

1. An *Acremonium cellulolyticus* strain that is *Acremonium cellulolyticus* CF-2612 (FERM BP-10848), characterized by (A) higher cellulase activity than *Acremonium cellulolyticus* C1 (FERM P-18508 and (B) hemicellulase activity, wherein (i) said cellulase activity comprises at least FPase, CMCase, avicelase and cellobiase and (ii) said hemicellulase activity comprises at least arabinanase and/or arabinofuranosidase.

2. A method for producing cellulase and/or hemicellulase, comprising culturing the *Acremonium cellulolyticus* strain of claim 1, which is a cellulase and hemicellulase-producing fungus, in a culture medium, and collecting the cellulase and/or hemicellulase from the culture medium.

3. A method for saccharifying biomass, comprising culturing the *Acremonium cellulolyticus* strain of claim 1, which is a cellulase and hemicellulase-producing fungus, in a culture medium, and saccharifying or degrading the biomass in the culture medium containing cellulase and/or hemicellulase.

4. The method according to claim 2, wherein the carbon source used in the medium is selected from the group consisting of powdery cellulose, avicel, cellobiose, filter papers, general papers, waste papers, wood, wheat bran, straw, rice straw, rice husks, bagasse, soybean cake, soybean curd residues, coffee bean residues, rice bran, lactose, lactose hydrate, whey, dairy products, hydrolysis products thereof obtained by hydrolysis treatment with acids or enzymes, and mixtures thereof.

5. The method according to claim 2, wherein the culture is a liquid culture or a solid culture.

6. A method for degrading or saccharifying biomass, comprising degrading or saccharifying the biomass using cellulase and/or hemicellulase obtained by the method of claim 2.

7. The method according to claim 3, wherein the carbon source used in the medium is selected from the group consisting of powdery cellulose, avicel, cellobiose, filter papers, general papers, waste papers, wood, wheat bran, straw, rice straw, rice husks, bagasse, soybean cake, soybean curd residues, coffee bean residues, rice bran, lactose, lactose hydrate, whey, dairy products, hydrolysis products thereof obtained by hydrolysis treatment with acids or enzymes, and mixtures thereof.

8. The method according to claim 3, wherein the culture is a liquid culture or a solid culture.

9. The method according to claim 3, wherein the cellulase is FPase, CMCase, avicelase, cellobiose, or a mixture thereof.

10. The method according to claim 3, wherein the hemicellulase is arabinanase, arabinofuranosidase, or a mixture thereof.

* * * * *

UNITED STATES PATENT AND TRADEMARK OFFICE
CERTIFICATE OF CORRECTION

| | | |
|---|---|---|
| PATENT NO. | : 8,034,596 B2 | Page 1 of 1 |
| APPLICATION NO. | : 12/598694 | |
| DATED | : October 11, 2011 | |
| INVENTOR(S) | : Xu Fang et al. | |

It is certified that error appears in the above-identified patent and that said Letters Patent is hereby corrected as shown below:

Title page, item (73) should read as follows:
(73) Assignees: National Institute of Advanced Industrial Science & Technology, Tokyo (JP); Tsukishima Kikai Co., Ltd., Tokyo (JP)

Signed and Sealed this
Twentieth Day of December, 2011

David J. Kappos
*Director of the United States Patent and Trademark Office*